United States Patent [19]
Maekawa et al.

[11] Patent Number: 5,193,559
[45] Date of Patent: Mar. 16, 1993

[54] DENTAL CLEANING INSTRUMENT

[76] Inventors: Kiyoshi Maekawa, 1480 Greenbriar Dr., Mount Prospect, Ill. 60056; Timothy D. Ladd, 219 Rose Arbor La., Matthews, N.C. 28105

[21] Appl. No.: 877,694

[22] Filed: May 1, 1992

[51] Int. Cl.⁵ .............................................. A61C 15/00
[52] U.S. Cl. ......................................... 132/321; 87/13
[58] Field of Search ........................ 132/321, 323, 329; 87/6, 8, 9, 13; 57/210

[56] References Cited

U.S. PATENT DOCUMENTS

| | | | |
|---|---|---|---|
| 1,839,486 | 1/1932 | Lawton | 132/323 |
| 2,880,493 | 4/1959 | Mitchell | 87/6 |
| 2,936,670 | 5/1960 | Walter | 87/8 |
| 3,323,406 | 6/1967 | Mitchell | 87/8 |
| 3,789,858 | 2/1974 | Pesce | 132/321 |
| 3,830,246 | 8/1974 | Gillings | 132/321 |
| 4,265,258 | 5/1981 | Eaton | 132/321 |
| 4,583,564 | 4/1986 | Finkelstein et al. | 132/321 |
| 4,646,766 | 3/1987 | Stallard | 428/364 X |

Primary Examiner—Robert P. Swiatek
Assistant Examiner—Nicholas D. Lucchesi

[57] ABSTRACT

A dental cleaning instrument for cleaning the interproximal area between teeth is constructed with three threads of yarn. The first thread is initially supported on a first post and a second thread of yarn is supported on a second post. The third thread is wound on a bobbin and then interlaced around and between the first and second threads in a figure-8 pattern, while the first and second threads are simultaneously advanced in a direction normal to the plane in which the bobbin is moving. The resulting instrument consists of woven threads having a combined denier in the range of 480–1240, with superior spreadability and separation of ends.

19 Claims, 1 Drawing Sheet

FLOSS 30 IS PRIOR ART

FLOSS 30 IS PRIOR ART

DENTAL CLEANING INSTRUMENT

This invention relates to a dental cleaning instrument, and more particularly, to an elongated string-type or thread-type instrument for cleaning the interproximal area between closely spaced teeth and a method of making the instrument.

BACKGROUND OF THE INVENTION

The interproximal areas between teeth are frequently problem areas. Food particles and plaque tend to accumulate in those areas, and gum disease or other infections may result. Various types of toothbrushes, picks, and elongated strings or threads, such as dental floss and dental tape, have been designed and used to combat this problem. Dental floss and dental tape have been found most useful as home remedies, but each has disadvantages. Dental floss usually consists of a single end, or a bundle of two or more ends of material interlaced together to form a combined denier in the 400–840 range. As used herein, the term "end" means one or more textile filaments having a high ratio of length to diameter. Dental floss fits easily between closely spaced teeth and into the interproximal areas, but the compactness of the floss is disadvantageous to cleaning, particularly in more widely spaced interproximal areas. Portions of the wider interproximal areas are not always wiped clean by the compact dental floss because, among other reasons, the compact construction reduces the overall surface area of the floss available to wipe and clean tooth surfaces.

Dental tape, on the other hand, usually is heavier than floss and has a denier in excess of 1240. Dental tape is usually constructed from a flat plastic film or ribbon formed in a manner to maintain its width at all times and to prevent the separation of its ends. For this reason, tape may be better for cleaning the interproximal area, but its breadth makes tape difficult to pass between closely spaced teeth. A user, therefore, may not even be able to wedge dental tape between closely spaced teeth into the interproximal areas.

Thus, there is a need for a dental instrument that can easily pass between closely spaced teeth and still effectively clean the interproximal area. Accordingly, an object of the invention is to provide a novel means for and method of constructing a dental instrument capable of easily gliding between closely spaced teeth and more effectively cleaning the interproximal area.

SUMMARY OF THE INVENTION

The objects of the invention are accomplished with at least three threads of yarn. As used herein, the term "thread" means one or more ends of yarn. The threads are woven together by mounting one thread on each of two posts, with the third thread wound around a bobbin. The bobbin is mounted on a carrier which moves in a plane normal to the posts. The bobbin loosely weaves the third thread around the posts and the other two threads in a figure-8 pattern. Each thread is composed of multiple nylon filaments. The resulting woven floss has a denier in the range of 480–1240. This construction promotes the spreadability and separation of the ends during use to provide better cleaning, and yet is compact enough to easily fit between teeth.

The above, as well as other objects and advantages of the invention, will become apparent from the following detailed description in which reference is made to the accompanying drawings.

DETAILED DESCRIPTION OF THE INVENTION

A dental instrument according to the invention uses at least three threads of yarn, and preferably each thread is composed of two ends of 140 denier, 68 filament nylon yarn. A suitable yarn is Monsanto $CO_2$ first quality, bright high tenacity yarn.

Figure 1:
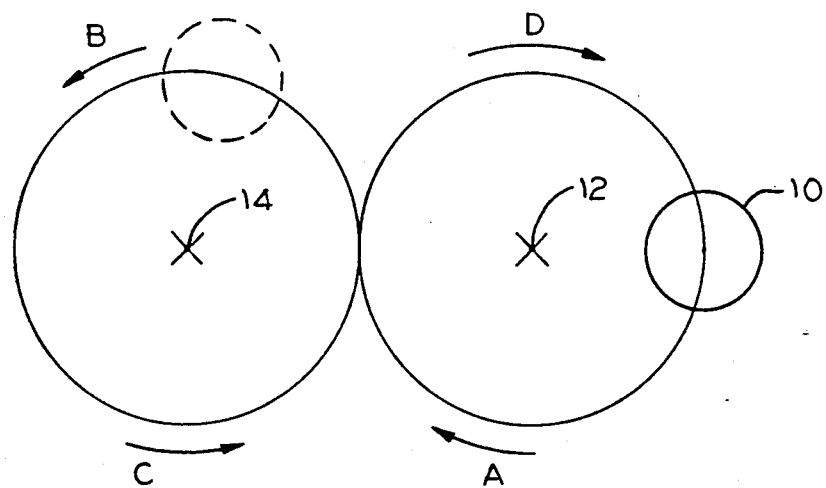
FIG. 1 is a schematic view of the weaving process of the invention.

As shown in FIG. 1, the threads of yarn are woven using a Steeger or NE Butt machine having a single carrier with a yarn bobbin 10 and two spaced, parallel posts 12, 14. Each post supports at least one thread of yarn, and each thread preferably includes two ends of equal predetermined lengths. The bobbin carries at least one thread of yarn, preferably including two ends (referred to as the "carrier thread"), and travels in a plane normal to the posts 12, 14. The bobbin carries the third thread around the posts and the other two threads in a figure-8 pattern, as indicated by arrows A, B, C and D, where arrow A marks the path for the first quarter of the bobbin's cycle, arrow B marks the path for the second quarter of the cycle, arrow C marks the path for the third quarter of the cycle, and arrow D marks the path for the fourth quarter of the cycle. The posts 12, 14 are located in the center of each of the two loops designated by arrows AD and BC. While the bobbin is interlacing the third thread around the other two threads, the threads on posts 12, 14 are advanced in a direction normal to the plane in which the bobbin 10 moves. This results in the third thread being woven or interlaced around and between the first and second ends for their entire lengths.

The resulting yarn bundle 20 desirably consists of 6 ends, each with a denier of 140, and a combined denier of 840. In contrast, a typical dental ribbon or tape, such as the product sold by Johnson & Johnson as DENTOTAPE, is constructed from 7 or 8 ends per post, 4 ends per carrier, and a combined denier of 1260 or 1400.

Figure 2:
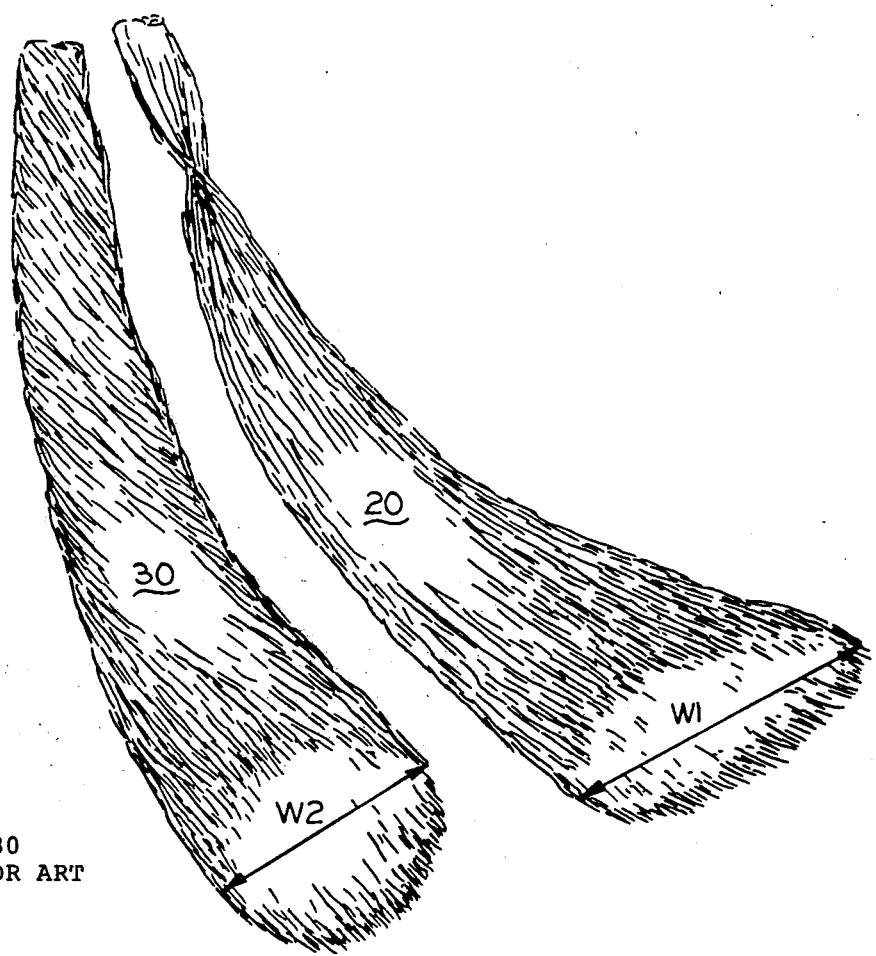
FIG. 2 is an enlarged view of the inventive floss and a typical prior art floss.

The invention is designed for the ends to spread and separate during use, which improves its cleaning effectiveness and comfort. As shown in FIG. 2, the inventive floss 20 has a width $W_1$ when applied to the interproximal area. The spreadability and than the width $W_2$ of a traditional dental floss 30 when it is applied to the interproximal area. The spreadability and separation of ends in the invention are furthered by providing a loose weave construction. A fidelity tensiometer #5669 is used to create between 0.5 and 1.4 pounds of tension on the yarn during weaving, resulting in between 2 and 3 picks per foot. By comparison, a typical dental ribbon or tape is made with 2.1 pounds of tension and 4 picks per foot. Dental tape is designed to prevent separation of its ends, because otherwise it would be too thick to use.

The relatively low picks per foot of the invention also keeps elongation of the floss at about 15.4%. The higher the elongation (stretch before breaking), the greater the orientation of the filament yarn bundle. As the filament yarn bundle orients, the diameter decreases. As the diameter decreases, the spreadability and plaque removal ability decreases. Therefore, the invention keeps the elongation factor low. By way of comparison, a typical dental ribbon or tape has an elongation factor of 15.7%.

The yarn take up roll, machine speed, and cycle time based on denier ratio for the invention are the same as that used for production of a typical dental ribbon or tape.

The inventive floss can be manufactured in a variety of constructions, all of which fall within a denier range of 480 to 1240. Using presently available deniers of nylon yarn, the possible constructions are as follows:

The inventive floss may be waxed. The threads receive an application of water insoluble wax, such as a 50/50 blend of paraffin microcrystalline wax, at a target pickup of 20% of the denier of the unwaxed ends. This is done in a manner well known in the art. This not only improves lubricity of the floss during use, but it also makes it easier to wind the product onto a coil with metered pre-determined lengths to accommodate packaging requirements.

If the floss is unwaxed, it has been found useful to apply to the threads a uniform topical coating of nylon type 651 resin targeted at a 4% pickup. A preferred construction for unwaxed floss is as follows:

TABLE A

| # ENDS ON CARRIER* | # ENDS ON EACH POST (2 POSTS) | TOTAL # ENDS | DENIER OF EACH END | TOTAL DENIER OF ENDS |
|---|---|---|---|---|
| 2 | 3 | 3 | 8 | 60 | 480 |
| 3 | 3 | 3 | 9 | 60 | 540 |
| 2 | 4 | 4 | 10 | 60 | 600 |
| 3 | 4 | 4 | 11 | 60 | 660 |
| 4 | 4 | 4 | 12 | 60 | 720 |
| 3 | 5 | 5 | 13 | 60 | 780 |
| 4 | 5 | 5 | 14 | 60 | 840 |
| 5 | 5 | 5 | 15 | 60 | 900 |
| 4 | 6 | 6 | 16 | 60 | 60 |
| 5 | 6 | 6 | 17 | 60 | 1020 |
| 4 | 7 | 7 | 18 | 60 | 1080 |
| 3 | 8 | 8 | 19 | 60 | 1140 |
| 4 | 8 | 8 | 20 | 60 | 1200 |
| 3 | 2 | 2 | 7 | 70 | 490 |
| 2 | 3 | 3 | 8 | 70 | 560 |
| 3 | 3 | 3 | 9 | 70 | 630 |
| 2 | 4 | 4 | 10 | 70 | 700 |
| 3 | 4 | 4 | 11 | 70 | 770 |
| 4 | 4 | 4 | 12 | 10 | 840 |
| 3 | 5 | 5 | 13 | 70 | 910 |
| 4 | 5 | 5 | 14 | 70 | 980 |
| 5 | 5 | 5 | 15 | 70 | 1050 |
| 4 | 6 | 6 | 16 | 70 | 1120 |
| 5 | 6 | 6 | 17 | 70 | 1190 |
| 1 | 2 | 2 | 5 | 100 | 500 |
| 2 | 2 | 2 | 6 | 100 | 600 |
| 3 | 2 | 2 | 7 | 100 | 700 |
| 2 | 3 | 3 | 8 | 100 | 800 |
| 3 | 3 | 3 | 9 | 100 | 900 |
| 2 | 4 | 4 | 10 | 100 | 1000 |
| 3 | 4 | 4 | 11 | 100 | 1100 |
| 2 | 1 | 1 | 4 | 140 | 560 |
| 1 | 2 | 2 | 5 | 140 | 700 |
| 2 | 2 | 2 | 6 | 140 | 840 |
| 3 | 2 | 2 | 7 | 140 | 980 |
| 2 | 3 | 3 | 8 | 140 | 1120 |
| 1 | 1 | 1 | 3 | 170 | 510 |
| 2 | 1 | 1 | 4 | 170 | 680 |
| 1 | 2 | 2 | 5 | 170 | 850 |
| 2 | 2 | 2 | 6 | 170 | 1020 |
| 3 | 2 | 2 | 7 | 170 | 1190 |
| 1 | 1 | 1 | 3 | 200 | 600 |
| 2 | 1 | 1 | 4 | 200 | 800 |
| 1 | 2 | 2 | 5 | 200 | 1000 |
| 2 | 2 | 2 | 6 | 200 | 1200 |
| 1 | 1 | 1 | 3 | 210 | 630 |
| 2 | 1 | 1 | 4 | 210 | 840 |
| 1 | 2 | 2 | 5 | 210 | 1060 |
| 1 | 1 | 1 | 3 | 235 | 705 |
| 2 | 1 | 1 | 4 | 235 | 940 |
| 1 | 2 | 2 | 5 | 235 | 1175 |
| 1 | 1 | 1 | 3 | 260 | 780 |
| 2 | 1 | 1 | 4 | 260 | 1040 |
| 1 | 1 | 1 | 3 | 280 | 840 |
| 2 | 1 | 1 | 4 | 280 | 1120 |
| 1 | 1 | 1 | 3 | 300 | 900 |
| 2 | 1 | 1 | 4 | 300 | 1200 |
| 1 | 1 | 1 | 3 | 315 | 945 |
| 1 | 1 | 1 | 3 | 400 | 1200 |

Note: *"#" means "number of"

| # ENDS ON CARRIER | # ENDS ON EACH POST (2 POSTS) | TOTAL # ENDS | DENIER OF EACH END | TOTAL DENIER OF ENDS |
|---|---|---|---|---|
| 1 | 2 | 2 | 5 | 140 | 700 |

The floss may also be impregnated with a flavoring agent. In that case, single ends of yarn are dye house dyed with FDA approved dyestuffs. Single ends are then woven using the above-described process.

Floss threads are typically white. The floss may be given a speckled or striped appearance by including one or more colored ends within the floss bundle as, for example, with the construction shown below:

| # ENDS ON CARRIER | # ENDS ON EACH POST (2 POSTS) | TOTAL # ENDS | DENIER OF EACH END | TOTAL DENIER OF ENDS |
|---|---|---|---|---|
| 2 colored | 2 colored  2 white | 6 | 100 colored  140 white | 680 |

While the principles of the invention have been described above in connection with specific embodiments, these descriptions are intended only by way of example and not as a limitation on the scope of the invention, which is stated more broadly in the appended claims. Therefore, the claims are to be construed to cover all equivalents.

The invention claimed is:

1. A dental cleaning instrument for cleaning or flossing the interproximal area between closely spaced teeth comprising:
   a first thread of predetermined length;
   a second thread extending parallel to said first thread of the same predetermined length;
   and a third thread interlaced around and between said first and second threads in a figure-8 pattern, said third thread interlaced along the entire length of said first and second threads to form a unitary construction of all three threads, said unitary construction having a denier in the range of 480–1240.

2. The dental cleaning instrument of claim 1 wherein said first thread comprises 2 ends of 140 denier each.

3. The dental cleaning instrument of claim 1 wherein said second thread comprises 2 ends of 140 denier each.

4. The dental cleaning instrument of claim 1 wherein said third thread comprises 2 ends of 140 denier each.

5. The dental cleaning instrument of claim 1 wherein said first, second, and third threads are each composed of two ends of 140 denier each.

6. The dental cleaning instrument of claim 1 wherein said threads are coated with wax.

7. The dental cleaning instrument of claim 6 wherein said threads are coated with wax at a pickup of 20% of the denier of the unitary construction.

8. The dental cleaning instrument of claim 1 wherein said threads are impregnated with a flavoring agent.

9. The dental cleaning instrument of claim 1 wherein said threads are interlaced at 2–3 picks per foot.

10. The dental cleaning instrument of claim 1 wherein said unitary construction has 15.7% elongation.

11. The dental cleaning instrument of claims 9 or 10 whereby said threads spread and separate when used in the interproximal area.

12. The dental cleaning instrument of claim 1 wherein at least one of said threads is different in color than said other threads.

13. A dental cleaning instrument for cleaning or flossing the interproximal area between closely spaced teeth comprising:
    a first pair of ends of yarn of predetermined length;
    a second pair of ends of yarn extending parallel to said first pair of ends of the same predetermined length;
    and a third pair of ends of yarn interlaced around and between said first and second pairs in a figure-8 pattern, said third pair interlaced along the entire length of said first and second pairs to form a unitary construction of all three pairs, said unitary construction having a denier in the range of 480–1240.

14. A method of forming a dental cleaning or flossing instrument, comprising:
    supporting a first thread of yarn of predetermined length on a first post and a second thread of yarn of the same predetermined length on a second post spaced from and parallel to said first post;
    winding a third thread of yarn on a yarn bobbin, said bobbin mounted for movement in a plane normal to said first and second posts;
    weaving said third thread of yarn around said first and second threads in a figure-8 pattern by advancing said bobbin around said posts, said weaving resulting in all three threads being tied together; and
    simultaneously advancing said first and second threads in a direction normal to said plane in which said bobbin travels so that said third thread is woven around and between said first and second threads for their entire length, said three threads having a combined denier in the range of 480–1240.

15. The method of claim 14 wherein said first and second threads are advanced at a rate so that said three threads are woven at 2–3 picks per foot.

16. The method of claim 15 wherein said threads are woven with a fidelity tensiometer rating of between 0.5–1.4 pounds of tension.

17. The method of claim 14 including the additional preliminary step of coating at least one of said threads with wax.

18. The method of claim 14 including the additional preliminary step of coating at least one of said threads with a mixture of wax and flavoring agent.

19. The method of claim 14 including the additional preliminary step of coating at least one of said threads with a mixture of wax, flavoring agent, and colored dye.

* * * * *

UNITED STATES PATENT AND TRADEMARK OFFICE
CERTIFICATE OF CORRECTION

PATENT NO. : 5,193,559

DATED : March 16, 1993

INVENTOR(S) : Kiyoshi Maekawa and Timothy D. Ladd

It is certified that error appears in the above-identified patent and that said Letters Patent is hereby corrected as shown below:

Col. 2, lines 50, 51, after "interproximal area," insert

--which is significantly larger than the width $W_2$ of a traditional dental floss 30 when it is applied to the interproximal area.--

Signed and Sealed this

Seventh Day of December, 1993

Attest:

BRUCE LEHMAN

Attesting Officer

Commissioner of Patents and Trademarks